US00PP14400P39

(12) United States Plant Patent

Kumar et al.

(10) Patent No.: US PP14,400 P3
(45) Date of Patent: Dec. 23, 2003

(54) ROSE SCENTED GERANIUM PELARGONIUM GRAVEOLENES PLANT 'SAFAL'

(50) Latin Name: *Pelargonium graveolensl*
Varietal Denomination: Safal

(75) Inventors: Sushil Kumar, Uttar Pradesh (IN); Ritika Gupta, Uttar Pradesh (IN); Kakaraparthi Pandu Sastry, Uttar Pradesh (IN); Suchitra Banerjee, Uttar Pradesh (IN); Gopal Rao Mallavarapu, Uttar Pradesh (IN); Srinivas Iyer Ramesh, Uttar Pradesh (IN); Ajit Kumar Shasany, Uttar Pradesh (IN); Mahendra Pandurang Darokar, Uttar Pradesh (IN); Suman Preet Singh Khanuja, Uttar Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/799,880

(22) Filed: Mar. 7, 2001

(65) Prior Publication Data

US 2003/0014799 P1 Jan. 16, 2003

(51) Int. Cl.[7] ..... A01H 5/00

(52) U.S. Cl. ..... Plt./324

(58) Field of Search ..... Plt./324

(56) References Cited

U.S. PATENT DOCUMENTS

PP12,425 P2 * 2/2002 Kulkarni et al. ..... Plt./258
PP12,457 P2 * 3/2002 Trees ..... Plt./324

* cited by examiner

*Primary Examiner*—Kent Bell
(74) *Attorney, Agent, or Firm*—Rothwell Figg Ernst & Manbeack

(57) ABSTRACT

The invention relates to a new, distinct and unique plant of rose scented geranium *Pelargonium graveolens* 'Safal' derived from a rare seed-set in cultivar 'Bipuli,' apparently the result of hybridization between largely sterile populations of the cultivar accessions 'Bipuli' and 'Hemanti', possessing the following combination of characteristics namely demonstrated vigour in the essential oil yield related traits in great measure and out yielded all the other accessions; the essential oil of the plant has 89% rhodinol content in which citronellol to geraniol ratio is approximately 1:1 and the contents of isomenthone, menthone, 10-epi-γ-eudesmol, 6,9-guaiadiene, decanoic acid and isodecanoic acid were relatively lower than in the oils of accessions 'Bipuli' and/or 'Hemanti', this plant can be propagated vegetatively through stem cuttings and suitable for commercial cultivation in large scale.

2 Drawing Sheets

Latin name of the plant claimed: The plant claimed is *Pelargonium graveolens* var. 'Safal'.

FIELD OF INVENTION

The present invention is related to the development of a novel high essential oil producing plant obtained through a unique method of progeny screening from the seeds obtained from the plant cultivar 'Bipuli' (unpatented) of *Pelargonium graveolens,* from which a novel, unique and commercially viable plant of rose scented geranium *Pelargonium graveolens* with high quantity and quality of essential oil yield was screened out. Further, the invention relates to the development of a high essential oil yielding hybrid named as 'Safal' through a planned selection and analysis of the 'Bipuli' seedling progenies. The essential oil of the plant is rich in rhodinol (89%) which includes the constituents geraniol, citronellyl, geranyl acetate, citronellyl acetate, geranyl formate, citronellyl formate, phenyl ethyl alcohols, cis and trans rose oxides, linalool and likewise. The hybrid of the invention can be planted and maintained for commercial cultivation through vegetative propagation using the stem cuttings.

BACKGROUND OF THE INVENTION

The members of the genus, Pelargonium commonly known as geraniums, are common ornamental plants. Some of the species such as *P. graveolens* are used as the source of rose scented geranium essential oil of considerable commercial importance. Geranium oil is one of the expensive essential oils used in perfumery, cosmetics and soap industries. On account of its antimicrobial and pesticidal activities, the use of geranium essential oil for technical applications is expanding. There is need to expand the geranium cultivation in diverse geographical areas with suitable agroclimates to meet the increasing industrial demand for the geranium essential oil. Traditionally, the geranium cultivation is confined to areas having semi-temperate to temperate climates where geranium is planted as perennial crop, maintained in the field for 4–5 years. The shoot portion of the perennial plantations of geranium is harvested 1 to 3 times each year to distill the oil. The spread of geranium cultivation has been narrow because the prevalent cultivars of *Pelargonium graveolens* are highly susceptible to water logging in soil, white ants and several bacterial and fungal diseases. Also there is paucity of genetic resources in Pelargonium species cultivated for essential oils. The available varieties suffer from high degree of male and female sterility. Breeding programmes based on cross hybridization have been scarce among essential oil yielding geraniums. So it is important to generate more genotypes with varied characters which can yield high quantity and quality of essential oil.

OBJECTS OF THE INVENTION

The main object of the present invention is to develop a new and distinct plant of *Pelargonium graveolens* 'Safal', through progeny screening from the seeds obtained from the plant cultivar 'Bipuli' of *Pelargonium graveolens,* said plant capable of producing higher quantity and quality of essential oil.

Another object of the present invention is to develop a new plant, which produces less of isomenthone, menthone and other sesqui-terpenes but rich in total rhodinol with a citroniol:geraniol ratio of 1:1.

DESCRIPTION OF THE INVENTION

Accordingly, in the present invention we have developed a novel, distinct, unique, and high essential oil yielding plant of geranium (*Pelargonium graveolens*) 'Safal', through progeny screening from the seeds obtained from the plant cultivar 'Bipuli' of *Pelargonlum graveolens,* possessing the following combination of characters:

a. the plant is a hybrid between cultivar 'Bipuli' and cultivar 'Hemanti' (unpatented) as the pollen donor as indicated by the co-dominance RAPD pattern obtained by the random primer 5'AACGTACGCG3' [SEQ ID NO:5]

b. possessing very large, hairy, soft, yellow-green (upper surface—144A; lower surface—147B) leaves, dark pink (78D) petals in the flowers, c. possessing vigorous and rapid vegetative growth with higher plant height of up to 82±6 cm, higher canopy size of up to 1.42±0.4 $m^2$, higher herb yield of up to 11.1±0.9 kg per plant, higher leaf area of up to 101±16 $cm^2$, higher oil content up to 0.35 to 0.40% and higher oil yield of up to 41 g/plant, d. producing an essential oil with the following composition; Citronellol 30.6±3.0, Geraniol 28.7±6.0, Isomenthone 8.4±0.5, Linalool 4.7±0.1, Cis rose oxide 0.4±0.1, trans rose oxide 0.2±0.1, Menthone 0.2±0.1, Citronellyl formate 6.6±0.5, Geranyl formate 2.9±0.2, 10-epi-γ-eudesmol 5.4±0.3, 6,9-guaiadiene 0.1±0.1, Decanoic acid 0.1±0.1, Phenyl ethyl tiglate 0.8±0.1, which may not be construed to be limited to these values, e. with distinct molecular profile by random amplified polymorphic DNA (RAPD) using 10 random primers (AAATCGGAGC [SEQ ID NO:1], GTCCTACTCG [SEQ ID NO:2], TGCGCGATCG [SEQ ID NO:4], AACGTACGCG [SEQ ID NO:5], CGGGATCCGC [SEQ ID NO:9], GCGAATTCCG [SEQ ID NO:10], CCCTGCAGGC [SEQ ID NO:11], CCAAGCTTGC [SEQ ID NO:12], AAGATAGCGG [SEQ ID NO:15], GGATCTGAAC [SEQ ID NO:16]) distinguishing the plant from the other existing varieties known to us, f. producing highest herbage, oil yield per plant as compared to any other existing varieties, and g. possessing the following botanical details.

Stem shape: Rounded.
Stem habit: Ramified.
Number of nodes:
(*i*) *Primary nodes.*—4.
(*ii*) *Secondary nodes.*—25 to 30.
(*iii*) *Tertiary nodes.*—7.
Average length of primary internode: 3.0 cm.
Leaf apex shape: Mucronate (rounded), cuspidate.
Leaf shape: Palmately lobed, cordate.
Leaf lamina base shape: Hastate.
Petiole shape: Long, hairy.
Petiole color: Yellow-green 147B.
Color of upper leaf surface: Yellow green (144A).
Color of lower leaf surface: Yellow green (147B).
Leaf length: 10.0 cm.
Leaf width: 13 cm.
Number of trichomes: 3.5/$mm^2$.
Trichome ratio (lower leaf/upper leaf): 2:1.
Peduncle:
*Length.*—5.5.
*Color.*—Yellow green (147B).
Time for flowering: February end.
Lastingness of bloom: Starts from February lasts till April.
Flower shape: Tubular.
Pedicel length: 2.5 mm.
Pedicel color: Yellow green (147B).
Calyx diameter: 5 mm.
Calyx:
*Color* (*both surfaces*).—Yellow green (146A).
*Sepal number.*—5.
*Shape.*—Triangular.
*Apex.*—Acute.
*Base.*—Concave.
*Margin.*—Entire, hairy.
*Length.*—0.7 cm.
Corolla:
*Petal number.*—5.
*Shape.*—Tubular bi-lipped free, zygomorphic.
*Apex.*—Slightly notched.
*Base.*—Slightly ligulate.
*Margin.*—Entire.
*Length* (*upper lip*).—1.0 cm.
*Length* (*lower lip*).—0.9 cm.
Corolla color (both surfaces): Purple group 78D.
Pubescence of corolla: Absent.
Reproductive organs:
*Androecium.*—10 stamens, filament sub-equal, united at base, anthers 7, dithoecous, versatile.
*Gynoceium.*—Pentacarpellary syncarpous superior ovary.
Color of stigma: Magenta (red purple) (78B).
Umbel:
*Inflorescence/plant.*—23.
*Flowers/inflorescence.*—7.
*Umbel shape.*—Umbrella.
Mature plant:
*Height.*—82 cm.
*Width.*—140 cm.
Susceptibility to disease: Susceptible to stem and root rot by fungus *Fusarium oxysporum, Rhyzoctonia solanii* and Pythium spp. and to termite attack.
Age of plants when described: 2 years (Lucknow, India).
Conditions of culture: Subtropical climate, soil sandy loam, alkaline (pH 7.8), low in available nitrogen (N 155 kg/ha), medium in available phosphorus ($P_2O_5$ 30.4 kg/ha) and exchangeable potassium ($K_2O$ 120 kg/ha). Field was dressed with manure @ 1 ton/ha and chlorphyriphos 1%/ha before planting of cuttings.
Asexual reproduction: Stem cuttings of about 10–20 cm length, with 4–5 nodes and a terminal bud, were planted in nursery beds or pots containing course sand/sphagnum moss. These rooted within 60 days and were planted in the field beds, without disturbing the root system, at 60×60 cm spacing.

Fruit/seed: Fruit setting did not take place in subtropical climatic conditions of Lucknow.

Time to produce finished plant: One month from rooted cutting to flowering.

The plant 'Safal' can yield more essential oil with less of isomenthone, menthone and other sesqui-terpenes but rich in total rhodinol with a citroniol:geraniol ratio of 1:1, than the prevailing cultivars now grown in India.

While observing large populations of the 'Bipuli', 'Hemanti' and 'Kunti' (unpatented) cultivars of rose scented geranium *P. graveolens* growing at the Kodaikanal field station Tamil Nadu, India of this Institute, in the temperate climate of Southern hills, formation of fruits bearing seeds at low frequency was observed in the populations of the 'Bipuli' cultivar of *P. graveolens*. It was realized that the seeds obtained may be the product of rare self fertilization within 'Bipuli' cultivar or cross pollination of 'Bipuli' gynoecia by fertile pollen grains formed on 'Hemanti' or 'Kunti' cultivar. The present work was carried out to reveal new genetic variation if any present, among the plants that could be raised from the spontaneous seeds borne on the plants of the 'Bipuli' cultivar. Comparison of the plants produced from seeds, collected from 'Bipuli' cultivar plants growing amongst those of 'Hemanti' and 'Kunti' cultivar, has shown that the 'Bipuli' seed progeny plants indeed differed from the plants of the three cultivars of *P. graveolens*. Out of all progenies, one (BSP-4) named as 'Safal' was found to be high yielding with essential oil containing the oil constituents in desirable proportions, novel and was thus the plant of this invention. As used herein, the accession number "BSP-4" and variety name 'Safal' are used interchangeably.

All the color grouping given in the description are made as per The International Royal Horticultural Society Colour chart.

BRIEF DESCRIPTION OF THE ACCOMPANYING DRAWINGS

BREEDING HISTORY

Figure 1:
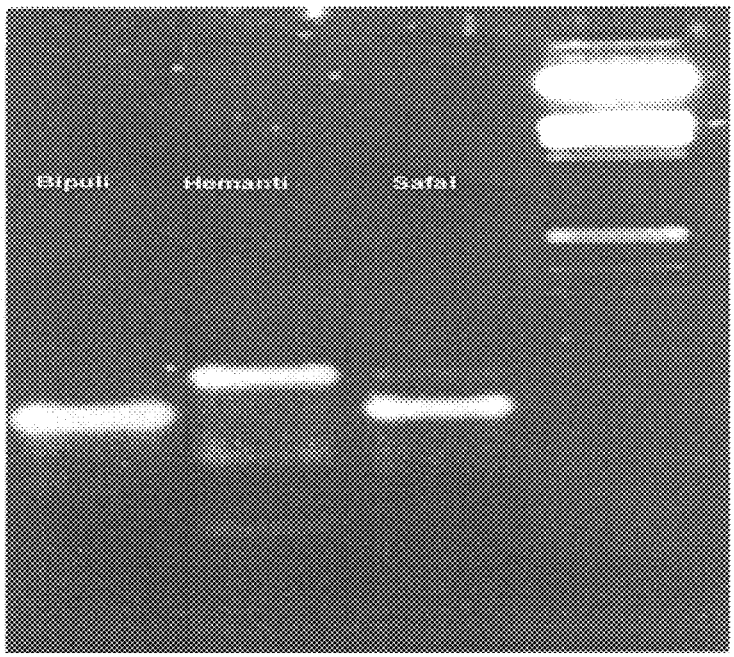
FIG. 1 shows Co-dominance pattern of RAPD profile for the plant 'Safal' with Primer 5'AACGTACGCG3' [SEQ ID NO:5].

The plants of 'Bipuli', 'Kunti' and 'Hemanti' varieties of *P. graveolens* were planted in beds of 20 $m^2$ size arranged randomly in a field at the experimental farm of Central Institute of Medicinal and Aromatic Plants (CIMAP), located at Kodaikanal at 101° N latitude, 78° E longitude and 1800 m above sea level in the state of Tamil Nadu, India, having temperate agroclimatic features. The distinguishing characteristics of the three accessions (varieties) are given in the Table 1. Table 2 gives the detailed botanical description of the newly developed plant 'Safal'. The flowers of all the three varieties were generally sterile, however a small number of fruits bearing seed were found to have come up in the year 1997 on the plants of the 'Bipuli' cultivar. The seeds were separated from the fruits, soaked in 100 ppm $GA_3$ solution in water for 24 hours and sown in earthen trays containing 1:1 ratio of soil and farmyard manure in a glasshouse at Lucknow, India (26.5° N 80.5° E and of 120 m altitude, in subtropical north Indian plains), India. Altogether four seedlings were recovered from three separate sowings of 10 seeds each. The seedlings were transplanted individually into pots carrying soil and sand mixture and were continued to be maintained in the glasshouse under 16 hour light and 8 hour dark conditions. Cuttings from these were used to multiply the new accessions called BSP-1 (unpatented), BSP-2 (unpatented), BSP-3 (unpatented) and BSP-4 ('Safal,' the subject of the present application) (BSP= Bipuli seed progeny).

TABLE 1

Distinguishing features of the cultivars Bipuli, Hemanti and Kunti compared to the Bipuli seed progenies.

| SI. No. | Character | Cultivar accessions cv. Bipuli | cv. Hemanti | cv. Kunti |
|---|---|---|---|---|
| 1. | Habit | Semi-erect | Prostrate | Erect |
| 2. | Canopy | Spread has 100 cm diameter and 50 cm height | Spread has 80 cm diameter and 55 cm height | Spread has 60 cm diameter and 40 cm height |
| 3. | Stem | Moderately hairy, strong, 4–5 primary branches which give out 20–25 secondary branches and 5–7 tertiary branches | Highly hairy, weak, 2–3 primary branches which are highly branched into 25–30 secondary branches, 5 tertiary branches | Poorly haired, sturdy usually 1–2 primary branches which bear 15–20 secondary branches and 3–5 tertiary branches |
| 4. | Leaf petiole | Medium size, thin rough dark pink at base | Long, thin, soft, light pink at base | Small, stout, rough, anthocyanin pigment absent |
| 5. | Leaf lamina | Small (5 cm long and 6 cm wide), lamina has about 75 lobes, hairy, yellowish green 146A[a] | Large (8 cm. long, 12 cm wide), lamina has about 60 lobes, very hairy, dark green 137B[b] | very large (9 cm long and 14 cm wide), lamina has 45 lobes, leathery, yellowish green 146A[a] |
| 6. | Leaf trichomes | Medium (400 μm), thin | Long (800 μm), thin | Short (300 μm), stout |
| 7. | Flower | Medium size ((1.5 cm), dark pink petals (78C[c]), yellow fertile anthers, seeds formed occasionally | Big size (1.5–2.0 cm), pink petals (80B[d]), anthers. incompletely developed in the form of staminodes | small size (1.0 cm), petals, light pink (74D[e]), pink. fertile anthers, seeds formed |
| 8. | Shoot essential oil content | 0.20–0.25% | 0.10–0.15% | 0.25–0.30% |
| 9. | Physical appearance of oil | Bright yellow | Pale yellow greenish yellow | Greenish yellow |
| 10. | Citronellol: geraniol ratio | 1:1 like in Bourbon type commercial oil of Reunion Island origin | 3–4:1 like that in commercial oil of Chinese origin | 1:5 |

| SI. No. | Character | Bipuli seed progeny accessions BSP-1 | BSP-2 |
|---|---|---|---|
| 1. | Habit | Erect | Erect |
| 2. | Canopy | Spread has 42 cm diameter and 48 cm height | Spread has 40 cm diameter and 45 cm height |
| 3. | Stem | Poorly haired, sturdy, 3 primary branches which give out 15–20 secondary and 3 tertiary branches | Poorly haired, sturdy, 3–4 primary branches which give out 10–50 secondary branches and 3–4 tertiary branches |
| 4. | Leaf petiole | Short, stout, rough, faint, anthocyanin present at the base | Very short, stout, rough, light pink at the base |

TABLE 1-continued

Distinguishing features of the cultivars Bipuli, Hemanti and Kunti compared to the Bipuli seed progenies.

| | | | |
|---|---|---|---|
| 5. | Leaf lamina | Large (9 cm long and 12 cm wide), lamina has 75 lobes, leathery, yellowish green 146A[a] | Large (9 cm long and 12 cm wide), lamina has 80 lobes, leathery, yellowish green |
| 6. | Leaf trichomes | Very short (250 μm), stout | Very short (200 μm), stout |
| 7. | Flower | Medium size 1.3 cm), pink petals (74B[e]), pink fertile, anthers, seeds formed | Medium size (1.3 cm), purple petals (77C[c]), pink fertile anthers, seeds formed |
| 8. | Shoot essential oil content | 0.31–0.35% | 0.35–0.40% |
| 9. | Physical appearance of oil | Greenish yellow | Greenish yellow |
| 10. | Citronellol: geraniol ratio | 1:3 | 1:2.5 |

| SI. | | Bipuli seed progeny accessions | |
|---|---|---|---|
| No. | Character | BSP-4 | BSP-4 ('Safal') |
| 1. | Habit | Erect | Semi-erect |
| 2. | Canopy | Spread has 68 cm diameter and 52 cm height | Spread has 140 cm diameter and 82 cm height |
| 3. | Stem | Moderately hairy, weak, 3 primary branches which give out 15–20 secondary branches and 3–5 tertiary branches | Moderately hairy, sturdy, 5 primary branches which are highly branched into 35–40 secondary branches and 5–7 tertiary branches |
| 4. | Leaf petiole | Long, thin soft, without any pigmentation at base | Very long, soft pink at the base |
| 5. | Leaf lamina | Medium (8 cm long and 10 cm wide) lamina has 60 lobes, soft, yellowish green 144A[a] | Very large (10 cm long and 13 cm wide), lamina has 60 lobes, hairy, soft, green 137C[b] |
| 6. | Leaf trichomes | Short (300 μm), thin | Medium (350 μm), thin |
| 7. | Flower | Small size (1 cm), light pink petals (74D[e]) , yellow anthers, seeds not formed | Medium size (1.3 cm) dark pink petals (78D[c]), yellow anthers seeds occasionally formed |
| 8. | Shoot essential oil content | 0.25–0.30% | 0.35–0.40% |
| 9. | Physical appearance of oil | Bright yellow | Pale yellow |
| 10. | Citronellol: geraniol ratio | 1.5:1 | 1:1 |

[a]yellow green group;
[b]green group;
[c]purple group;
[d]purple violet group;
[e]red purple group;
*(all color groupings were made as per The Royal Horticultural Society Colour Chart)

TABLE 2

Detailed Botanical Description of the plant 'Safal':

| | | |
|---|---|---|
| 1. | Stem shape: | ROUNDED |
| 2. | Stem habit: | RAMIFIED |
| 3. | Number of nodes | |
| | (i) Primary Nodes: | 4 |
| | (ii) Secondary Nodes: | 25 to 30 |
| | (iii) Tertiary Nodes: | 7 |
| 4. | Average length of primary internode: | 3.0 cm |
| 5. | Leaf apex shape: | MUCRONATE (rounded), CUSPIDATE |
| 6. | Leaf shape: | PALMATELY LOBED, CORDATE |
| 7. | Leaf lamina base shape: | HASTATE |
| 8. | Petiole shape: | LONG, HAIRY |
| 9. | Petiole color: | YELLOW-GREEN 147B |
| | Color of Upper leaf surface: | YELLOW GREEN (144A) |
| 10. | Color of lower leaf surface: | YELLOW GREEN (147B) |
| 11. | Leaf length: | 10.0 cm |
| 12. | Leaf width: | 13 cm |
| 13. | Number of trichomes: | 3.5/mm$^2$ |
| 14. | Trichome ratio: (lower leaf/upper leaf) | 2:1 |
| 15. | Peduncle | |
| | length: | 5.5 |
| | color: | YELLOW GREEN (147B) |
| 16. | Time for flowering: | FEBRUARY END |
| 17. | Lastingness of bloom: | Starts from February lasts till April |
| 18. | Flower shape: | TUBULAR |
| 19. | Pedicel length: | 2.5 mm |
| 20. | Pedicel color: | YELLOW GREEN (147B) |
| 21. | Calyx diameter: | 5 mm |
| 22. | Calyx | |
| | (i) color (both surfaces): | YELLOW GREEN (146A) |
| | (ii) sepal number: | 5 |
| | (iii) shape: | triangular |
| | (iv) apex: | acute |
| | (v) base: | concave |
| | (vi) margin: | entire, hairy. |
| | (vii) length: | 0.7 cm |
| 23. | Corolla | |
| | (i) petal number: | 5 |
| | (ii) shape: | tubular bi-lipped free, zygomorphic |
| | (iii) apex: | slightly notched |
| | (iv) base: | slightly ligulate |
| | (v) margin: | entire |
| | (vi) length (upper lip): | 1.0 cm |
| | (vii) length (lower lip): | 0.9 cm |
| 24. | Corolla color (both surfaces): | Purple group 78D |
| 25. | Pubescence of corolla: | ABSENT |
| 26. | Reproductive organs | |
| | (i) androecium: | 10 stamens, filament sub-equal, united at base, anthers 7, dithoecous, versatile |
| | (ii) gynoecium: | pentacarpellary syncarpous superior ovary |
| 27. | Color of stigma: | MAGENTA (RED PURPLE) (78B) |
| 28. | Umbel | |
| | (i) inflorescence/plant: | 23 |
| | (ii) flowers/inflorescence: | 7 |
| | (iii) umbel shape: | umbrella |
| 29. | Mature plant | |
| | (i) height: | 82 cm |
| | (ii) width: | 140 cm |
| 30. | Susceptibility to disease: | susceptable to stem and root rot by fungus *Fusarium oxysporum*, *Rhyzoctonia solanii* and Pythium spp. and to termite attack |

Field Experiments

Out of these 4 progenies obtained, preliminary analysis revealed encouraging results for BSP-4, ('Safal'), as the plant showed high vigor in biomass production and higher oil yield. So the plant 'Safal' was taken to the field for further evaluation. To variously compare the 'Safal' accession with the cultivar accessions 'Bipuli', 'Hemanti' and 'Kunti', field plot experiments were carried out over two winter-summer cropping seasons (1998–1999) and (1999–2000) at the experimental farm of Central Institute of Medicinal and Aromatic Plants, at Lucknow India (26.5° N 80.5° E and of 120 m altitude, in subtropical north Indian plains). The soil in the field used was sandy loam in texture, alkaline in reaction (pH, 7.8), low in available N (155 kg/ha) and medium in available phosphorous (30.4 kg $P_2O_5$/ha) and exchangeable potassium (120 kg $K_2O$/ha). In October 1998, six glasshouse-grown plants of each accession were transferred to the field trial. The cuttings drawn from each of the 4 accessions were planted in randomized blocks replicated three times, in January 1999. The field blocks used were given a uniform dose of 100 kg/ha $P_2O_5$ and 60 kg/ha $K_2O$. Nitrogen was applied in three splits while phosphorus and potassium were applied at the time of planting. A light irrigation was given just after the planting of cuttings and plots were manually weeded and irrigated at regular interval of two weeks throughout the cropping season. The crops were allowed to grow until June when observations on the morphology of the plants were recorded and crops harvested to estimate the yield of herbage as well as yield and quality of essential oil. About 300 g sample of herbage harvested from each plot was distilled to determine its oil content. The oil samples were analyzed by GC, GC-MS procedures. The 4 accessions were similarly grown and assessed in the 1999–2000 winter-summer cropping season at Lucknow. The parameters on which observations were recorded were averaged for the two seasons for presentation in Tables 3 and 4.

TABLE 3

The variation observed in the expression of the essential oil yield related traits among 4 accessions in the rose scented geranium *Pelargonium graveolens*

| Acc. No. | Essential oil yield parameter | | | |
|---|---|---|---|---|
| | Plant height (cm) | Canopy Size ($m^2$) | Herb Yield (kg/plant) | Number of branches/plant |
| Bipuli | 50 ± 2 | 0.81 ± 0.1 | 3.3 ± 0.1 | 25 ± 2 |
| Hemanti | 55 ± 2 | 0.80 ± 0.2 | 3.9 ± 0.5 | 30 ± 4 |
| Kunti | 40 ± 4 | 0.58 ± 0.2 | 2.0 ± 0.1 | 22 ± 1 |
| BSP-4 ('Safal') | 82 ± 6 | 1.42 ± 0.4 | 11.1 ± 0.9 | 47 ± 4 |
| Mean ± (SEM) | 53 ± 5 | 0.73 ± 0.14 | 3.9 ± 1.3 | 27 ± 4 |
| CD at 5% | 5 | 0.30 | 0.6 | 4 |
| | Number of leaves/plant | Leaf/stem ratio (cm) | Leaf petiole lemgth (cm) | |
| Bipuli | 1437 ± 100 | 0.7 ± 0.1 | 9.7 ± 1.8 | |
| Hemanti | 1801 ± 167 | 0.9 ± 0.1 | 11.1 ± 1.4 | |
| Kunti | 1363 ± 177 | 1.2 ± 0.1 | 9.1 ± 1.1 | |
| BSP-4 ('Safal') | 4632 ± 201 | 0.9 ± 0.5 | 24.6 ± 2.8 | |
| Mean ± (SEM) | 2445 ± 500 | 1.0 ± 0.07 | 11.7 ± 2.3 | |
| CD at 5% | 697 | 0.2 | 3.8 | |

TABLE 3-continued

The variation observed in the expression of the essential oil yield related traits among 4 accessions in the rose scented geranium *Pelargonium graveolens*

| Acc. No. | Essential oil yield parameter | | |
|---|---|---|---|
| | Leaf Area ($cm^2$) | Oil Content % | Oil Yield/ plant (g/plant) |
| Bipuli | 70 ± 7 | 0.25 ± 0.1 | 8.2 ± 0.1 |
| Hemanti | 68 ± 2 | 0.20 ± 0.1 | 7.8 ± 0.2 |
| Kunti | 108 ± 5 | 0.3 ± 0.1 | 6.0 ± 0.5 |
| BSP-4 ('Safal') | 101 ± 16 | 0.37 ± 0.1 | 41.0 ± 0.9 |
| Mean ± (SEM) | 83 ± 6 | 0.29 ± 0.2 | 19.3 ± 8.0 |
| CD at 5% | 24 | 0.08 | 11.7 |

TABLE 4

The variation in the expression of essential oil quality among 4 accessions, in the rose scented geranium *Pelargonium graveolens*
% content of terpenoid in essential oil

| Accession | Citronellol | Geraniol | Iso-menthone | Linalool | Cis rose oxide |
|---|---|---|---|---|---|
| Bipuli | 34.5 ± 3.4 | 21.8 ± 3.3 | 7.7 ± 0.6 | 4.3 ± 1.6 | 0.6 ± 0.3 |
| Hemanti | 50.6 ± 1.4 | 1.2 ± 0.3 | 12.4 ± 0.7 | 1.1 ± 0.1 | 0.8 ± 0.1 |
| Kunti | 13.0 ± 1.0 | 43.7 ± 1.4 | 10.5 ± 0.7 | 6.6 ± 0.1 | 0.2 ± 0.1 |
| BSP-4 ('Safal') | 30.6 ± 3.0 | 28.7 ± 6.0 | 8.4 ± 0.5 | 4.7 ± 0.1 | 0.4 ± 0.1 |
| Means ± SEM | 26.2 ± 5.6 | 27.2 ± 6.2 | 9.5 ± 1.0 | 6.2 ± 1.3 | 0.3 ± 0.1 |
| CD at 5% | 6.5 | 4.3 | 1.9 | 2.7 | 0.3 |
| Accession | Trans rose oxide | Menthone | Citronellyl formate | Geranyl formate | 10-epi-γ-eudesmol |
| Bipuli | 0.3 ± 0.1 | 0.1 ± 0.1 | 7.8 ± 0.3 | 2.1 ± 0.2 | 5.7 ± 0.3 |
| Hemanti | 0.5 ± 0.1 | 0.1 ± 0.1 | 13.8 ± 0.8 | 0.2 ± 0.1 | 2.4 ± 0.2 |
| Kunti | 0.1 ± 0.1 | 0.2 ± 0.1 | 0.6 ± 0.1 | 0.2 ± 0.1 | 4.1 ± 0.1 |
| BSP-4 ('Safal') | 0.2 ± 0.1 | 0.2 ± 0.1 | 6.6 ± 0.5 | 2.9 ± 0.2 | 5.4 ± 0.3 |
| Means ± SEM | 0.2 ± 0.1 | 0.2 ± 0.1 | 4.5 ± 0.4 | 0.9 ± 0.4 | 3.7 ± 0.8 |
| CD at 5% | 0.1 | 0.1 | 1.0 | 0.5 | 0.5 |
| Accession | 6,9-guaiadiene | Decanoic acid | Isodecanoic | Phenyl ethyl tiglate | |
| Bipuli | 0.1 ± 0.1 | ND[a] | ND | 0.8 ± 0.3 | |
| Hemanti | 0.4 ± 0.1 | ND | ND | 0.8 ± 0.2 | |
| Kunti | 2.0 ± 0.1 | 2.8 ± 0.1 | 0.6 ± 0.2 | 0.9 ± 0.1 | |
| BSP-4 ('Safal') | 0.1 ± 0.1 | 0.1 ± 0.1 | ND | 0.8 ± 0.1 | |
| Means ± SEM | 1.8 ± 0.7 | 1.5 ± 0.7 | 0.4 ± 0.2 | 1.0 ± 0.6 | |
| CD at 5% | 0.1 | 0.1 | 0.1 | 0.5 | |

[a]ND = not detected

GC and GC-MS Analysis

GC analysis of the essential oils was performed on a Perkin-Elmer gas chromatograph 8500 equipped with FID, using two fused silica capillary columns BP-1 coated with dimethyl siloxane (30 m×0.25 mm×0.25 μm film thickness) and BP-20 coated with carbowax 20M (20 m×0.25 mm×0.25 μm thickness), carrier gas nitrogen at 10 psi inlet pressure and temperature programmed to 60–220° C. at 5° C./min. For BP-20 column and split ratio of 1:80. GC-MS was performed on Schimadzu QP-2000 instrument using ULBON. HR-1 fused silica column (50 m×0.25 mm×0.25 μm film thickness), temperature programmed to 100°–250°

C. at 10° C./min, carrier gas helium at 2 ml/min, MS conditions of El mode 70 eV and ion source temperature of 250° C.

Identification of the Compounds

Compounds were identified by comparing the retention indices (relative to C8–C21 alkanes) with those reported in literature by peak enrichment on coinjection with standards wherever possible and by comparison of mass spectra of the peak with those of compounds reported in literature (Jennings, W. & T. Shibamoto, 1980. Qualitative analysis of flavour and fragrance volatile by capillary GC, Academic Press Inc., New York.; Adams, R. P., 1990. Identification of essential oils by ion trap mass spectroscopy. Academic Press, San Diego, Calif.). Relative amounts of individual components were estimated based on peak areas on BP-1 column without FID response correction.

Molecular Analysis of Hybrids

DNA was isolated from young leaves (1 g) taken from mature plants following the reported protocol (Khanuja, S. P. S., Shasany, A. K., Darokar, M. P., and Kumar, S., 1999, Rapid isolation of PCR amplifible DNA from dry and fresh samples of plant producing large amounts of secondary metabolites and essential oil by modified CTAB procedure. Plant Molecular Biology, 17:74.) and was digested with EcoRI restriction endonucleases. A set of twenty decanucleotide primers (M/S Bangalore Genie, India) were used for PCR amplification. Polymerase chain reaction (PCR) was carried out in 25 $\mu$l reaction volume, containing 20–40 ng of plant genomic DNA, 125 $\mu$M Of $MgCl_2$ buffer, 100, $\mu$M of each dNTP, 5 p motes of primer and 0.2 units of Taq DNA polymerase. Amplification was carried out in DNA Engine PTC 200 (M J Research, USA) thermal cycler programmed for 45 cycles of 1 min at 94° C., 1 at 36° C. and 2 min at 72° C. The amplification cycle was concluded with final extension at 72° C. for 5 min. Amplification products were electrophoresed in 1.2% (w/v) agarose gel, visualized by ethidium bromide (0.5 $\mu gml^{-1}$) staining. The pictures of the gel were scanned for the presence of polymorphic fragments which were scored for the presence (+) or absence (−) of bands. The data so generated was used for calculating the index of genetic similarity using Nei and Li's matching co-efficient method (Nei, M. and Li, W. H., 1979. Mathematical model for studying genetic variation in terms of restriction endonuclease. Proc. Natl. Acad. Sci. U.S.A.,74 : 5267–5273.). The similarity indices were calculated by using the formula: Number of similar bands between the two accessions/total number of bands in the two accessions×2 and present in Table 5.

TABLE 5

Average similarity indices of 'Safal' with the cultivar accessions 'Bipuli', 'Hemanti' and 'Kunti' in rose scented geranium *Pelargonium graveolens*

| Accession | Bipuli | Hemanti | Kunti | Safal |
|---|---|---|---|---|
| Bipuli | 1.00 | | | |
| Hemanti | 0.81 | 1.00 | | |
| Kunti | 0.83 | 0.78 | 1.00 | |
| Safal | 0.76 | 0.75 | 0.67 | 1.00 |

The similarity indices arrived at using 20 decanucleotide primers (MAP01 to MAP20: AAATCGGAGC [SEQ ID NO:1], GTCCTACTCG [SEQ ID NO:2], GTCCTTAGCG [SEQ ID NO:3], TGCGCGATCG [SEQ ID NO:4], AACGTACGCG [SEQ ID NO:5], GCACGCCGGA [SEQ ID NO:6], CACCCTGCGC [SEQ ID NO:7], CTATCGCCGC [SEQ ID NO:8], CGGGATCCGC [SEQ ID NO:9], GCGAATTCCG [SEQ ID NO:10], CCCTGCAGGC [SEQ ID NO:11], CCAAGCTTGC [SEQ ID NO:12], GTGCAATGAG [SEQ ID NO:13], AGGATACGTG [SEQ ID NO:14], AAGATAGCGG [SEQ ID NO:15], GGATCTGAAC [SEQ ID NO:16], TTGTCTCAGG [SEQ ID NO:17], CATCCCGAAC [SEQ ID NO:19], GGACTCCACG [SEQ ID NO:19], AGC;CTGACGC [SEQ ID NO:20], respectively) in the RAPD analysis are given in the Table 4. Table 4 indicated that the accession 'Safal' was more similar to the parent varieties 'Bipuli' and 'Hemanti' (more than 75%) than 'Kunti' (67%). Further the RAPD profile of 'Safal' showed co-dominance inheritance from 'Bipuli' and 'Hemanti' (FIG. 1).

Distinctiveness of Safal

The accession 'Safal' expressed most of the characters at much higher levels than the corresponding measurements in the rest of the accessions. In 'Safal', the leaf/stem ratio and leaf area measurements fell within the ranges covered for these characters by the cultivar accessions. As compared to 'Bipuli', 'Safal' was 1.6 fold taller in height, had 1.7 fold larger canopy, yielded 3.5 fold more herbage, had 2 fold more branches, 3 fold more leaves, 3.5 fold longer leaf petiole, 1.4 fold more oil content in herbage and gave 5 fold more oil yield (Table 2). Apparently the accession 'Safal' demonstrated the kind of vigour associated with hybrids or transgressive segregants. The variation observed for the essential oil quality parameters among the seven accessions in terms of the 14 terpenoid components that could be identified are summarized in the Table 3. The oil of the accession 'Safal' had geraniol to citronellol proportion as 1:1 and had other parameters widely different from those observed for the oils of the other accessions. The cis and trans rose oxides and citronellyl fonnate contents in the oil of 'Safal' accession were lower than in the oils of the accessions 'Bipuli' and 'Hemanti'. The essential oil of the accession 'Safal' had low concentrations of 6,9-guaiadiene, decanoic acid and, isodecanoic acid, like in the oils of the accessions 'Bipuli' and 'Hemanti'. These observations described above have demonstrated that the accession 'Safal' of *P. graveolens* differed from the cultivar accessions 'Bipuli', 'Kunti' and 'Hemanti' not only in some of the morphological and essential oil characteristics but also in their DNA profiles.

The accession 'Safal' demonstrated the expression of essential oil yield related characters at much higher levels than by all the accessions studied. The terpenoid profile of the essential oil of the accession 'Safal' also appeared to be unique, in that it had equally high concentrations of citronellol and geraniol and very high concentration of total rhodinols. Considering all the essential oil yield related characters together with hierarchical relationships arrived at by DNA fingerprinting, it is possible to surmise that the accession 'Safal' may be a hybrid between the accession 'Bipuli' and 'Hemanti'. The accession 'Safal' is novel, unique and has highly useful combination of yield, essential oil quality related characteristics, and this can be used for commercial cultivation to extract high value essential oil having utility for industrial and pharmaceutical purposes. Finally, the new plant was selected for its high quality essential oil and the genotype can be used in the future for plant improvement. The accession BSP-4 is the plant of this invention and was named as 'Safal'.

Randomly Amplified Polymorphic DNA Analysis

Figure 2:
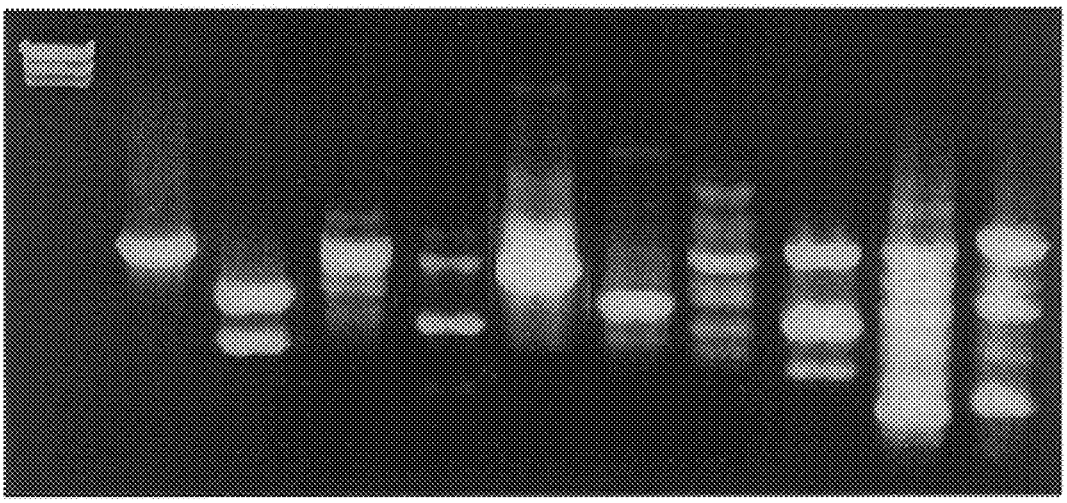
FIG. 2 shows Unique RAPD profile of 'Safal'.
Figure 3:
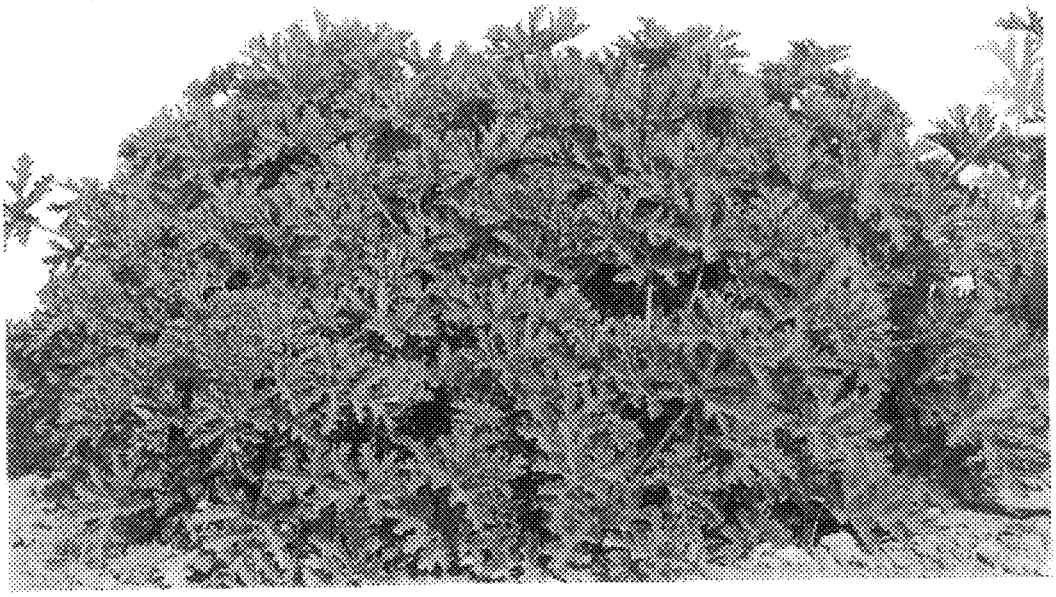
FIG. 3 is a Photograph of plant 'Safal'.

The RAPD profiles of the plant 'Safal' were unambiguously able to establish its distinct identity as completely different from the parent plant 'Bipuli' as well as the known varieties 'Kunti' and 'Hemanti'. The plant of the present invention was developed by screening the 'Bipuli' seed progenies and differentiated as distinct, unique and novel at DNA level. The plant is having desirable morphological and economical traits in a rare unmatchable combination and is available only with us in CIMAP. The primers with the sequence AAATCGGAGC [SEQ ID NO:1], GTCCTACTCG [SEQ ID NO:2], TGCGCGATCG [SEQ ID NO:4], AACGTACGCG [SEQ ID NO:5], CGGGATCCGC [SEQ ID NO:9], GCGAATTCCG [SEQ ID NO:10], CCCTGCAGGC [SEQ ID NO:11], CCAAGCTTGC [SEQ ID NO:12], AAGATAGCGG [SEQ ID NO:15], GGATCTGAAC [SEQ ID NO:16], were used to develop a unique and distinct RAPD profile of the Plant (FIG. 2). The whole plant 'Safal' has been shown in FIG. 3 wherein the canopy and the shape of the leaves are quite apparent.

SEQUENCE LISTING

```
<160> NUMBER OF SEQ ID NOS: 20

<210> SEQ ID NO 1
<211> LENGTH: 10
<212> TYPE: DNA
<213> ORGANISM: Artificial Sequence
<220> FEATURE:
<223> OTHER INFORMATION: Primer

<400> SEQUENCE: 1

aaatcggagc                                                          10


<210> SEQ ID NO 2
<211> LENGTH: 10
<212> TYPE: DNA
<213> ORGANISM: Artificial Sequence
<220> FEATURE:
<223> OTHER INFORMATION: Primer

<400> SEQUENCE: 2

gtcctactcg                                                          10


<210> SEQ ID NO 3
<211> LENGTH: 10
<212> TYPE: DNA
<213> ORGANISM: Artificial Sequence
<220> FEATURE:
<223> OTHER INFORMATION: Primer

<400> SEQUENCE: 3

gtccttagcg                                                          10


<210> SEQ ID NO 4
<211> LENGTH: 10
<212> TYPE: DNA
<213> ORGANISM: Artificial Sequence
<220> FEATURE:
<223> OTHER INFORMATION: Primer

<400> SEQUENCE: 4

tgcgcgatcg                                                          10


<210> SEQ ID NO 5
<211> LENGTH: 10
<212> TYPE: DNA
<213> ORGANISM: Artificial Sequence
<220> FEATURE:
<223> OTHER INFORMATION: Primer
```

-continued

<400> SEQUENCE: 5 aacgtacgcg 10

<210> SEQ ID NO 6
<211> LENGTH: 10
<212> TYPE: DNA
<213> ORGANISM: Artificial Sequence
<220> FEATURE:
<223> OTHER INFORMATION: Primer

<400> SEQUENCE: 6 gcacgccgga 10

<210> SEQ ID NO 7
<211> LENGTH: 10
<212> TYPE: DNA
<213> ORGANISM: Artificial Sequence
<220> FEATURE:
<223> OTHER INFORMATION: Primer

<400> SEQUENCE: 7 caccctgcgc 10

<210> SEQ ID NO 8
<211> LENGTH: 10
<212> TYPE: DNA
<213> ORGANISM: Artificial Sequence
<220> FEATURE:
<223> OTHER INFORMATION: Primer

<400> SEQUENCE: 8 ctatcgccgc 10

<210> SEQ ID NO 9
<211> LENGTH: 10
<212> TYPE: DNA
<213> ORGANISM: Artificial Sequence
<220> FEATURE:
<223> OTHER INFORMATION: Primer

<400> SEQUENCE: 9 cgggatccgc 10

<210> SEQ ID NO 10
<211> LENGTH: 10
<212> TYPE: DNA
<213> ORGANISM: Artificial Sequence
<220> FEATURE:
<223> OTHER INFORMATION: Primer

<400> SEQUENCE: 10 gcgaattccg 10

<210> SEQ ID NO 11
<211> LENGTH: 10
<212> TYPE: DNA
<213> ORGANISM: Artificial Sequence
<220> FEATURE:
<223> OTHER INFORMATION: Primer

<400> SEQUENCE: 11 ccctgcaggc 10

-continued

<210> SEQ ID NO 12
<211> LENGTH: 10
<212> TYPE: DNA
<213> ORGANISM: Artificial Sequence
<220> FEATURE:
<223> OTHER INFORMATION: Primer

<400> SEQUENCE: 12 ccaagcttgc 10

<210> SEQ ID NO 13
<211> LENGTH: 10
<212> TYPE: DNA
<213> ORGANISM: Artificial Sequence
<220> FEATURE:
<223> OTHER INFORMATION: Primer

<400> SEQUENCE: 13 gtgcaatgag 10

<210> SEQ ID NO 14
<211> LENGTH: 10
<212> TYPE: DNA
<213> ORGANISM: Artificial Sequence
<220> FEATURE:
<223> OTHER INFORMATION: Primer

<400> SEQUENCE: 14 aggatacgtg 10

<210> SEQ ID NO 15
<211> LENGTH: 10
<212> TYPE: DNA
<213> ORGANISM: Artificial Sequence
<220> FEATURE:
<223> OTHER INFORMATION: Primer

<400> SEQUENCE: 15 aagatagcgg 10

<210> SEQ ID NO 16
<211> LENGTH: 10
<212> TYPE: DNA
<213> ORGANISM: Artificial Sequence
<220> FEATURE:
<223> OTHER INFORMATION: Primer

<400> SEQUENCE: 16 ggatctgaac 10

<210> SEQ ID NO 17
<211> LENGTH: 10
<212> TYPE: DNA
<213> ORGANISM: Artificial Sequence
<220> FEATURE:
<223> OTHER INFORMATION: Primer

<400> SEQUENCE: 17 ttgtctcagg 10

<210> SEQ ID NO 18
<211> LENGTH: 10
<212> TYPE: DNA
<213> ORGANISM: Artificial Sequence
<220> FEATURE:
<223> OTHER INFORMATION: Primer -continued

<400> SEQUENCE: 18 catcccgaac 10

<210> SEQ ID NO 19
<211> LENGTH: 10
<212> TYPE: DNA
<213> ORGANISM: Artificial Sequence
<220> FEATURE:
<223> OTHER INFORMATION: Primer

<400> SEQUENCE: 19 ggactccacg 10

<210> SEQ ID NO 20
<211> LENGTH: 10
<212> TYPE: DNA
<213> ORGANISM: Artificial Sequence
<220> FEATURE:
<223> OTHER INFORMATION: Primer

<400> SEQUENCE: 20 agcctgacgc 10

What is claimed is:

1. A new and distinct plant of Geranium plant named 'Safal,' illustrated and described.

* * * * *